United States Patent
Varriale et al.

(10) Patent No.: US 11,971,466 B2
(45) Date of Patent: Apr. 30, 2024

(54) SYSTEM AND METHOD FOR FAT AND WATER DIAGNOSTIC IMAGING

(71) Applicant: Esaote S.p.A., Genoa (IT)

(72) Inventors: Rosario Varriale, Genoa (IT); Luca Balbi, Genoa (IT); Annamaria Carbone, Genoa (IT)

(73) Assignee: ESAOTE S.P.A., Genoa (IT)

( * ) Notice: Subject to any disclaimer, the term of this patent is extended or adjusted under 35 U.S.C. 154(b) by 0 days.

(21) Appl. No.: 17/490,338

(22) Filed: Sep. 30, 2021

(65) Prior Publication Data

US 2022/0107376 A1 Apr. 7, 2022

(30) Foreign Application Priority Data

Oct. 2, 2020 (IT) .................. 102020000023257

(51) Int. Cl.
*G01R 33/48* (2006.01)
*A61B 5/055* (2006.01)
(Continued)

(52) U.S. Cl.
CPC .......... *G01R 33/4828* (2013.01); *A61B 5/055* (2013.01); *G06T 7/0012* (2013.01);
(Continued)

(58) Field of Classification Search
CPC ... G01R 33/4828; A61B 5/055; G06T 7/0012; G06T 2207/10088; G06T 2207/20081; G06N 3/08
See application file for complete search history.

(56) References Cited

U.S. PATENT DOCUMENTS 4,720,679 A * 1/1988 Patrick ............. G01R 33/56527
324/309
5,909,119 A * 6/1999 Zhang ................ G01R 33/4828
324/309
(Continued)

FOREIGN PATENT DOCUMENTS

EP 1345154 A1 9/2003
EP 1586076 A2 10/2005
(Continued)

OTHER PUBLICATIONS

Wikipedia, "Category:Classification_algorithms", Dec. 6, 2016, Wikimedia Foundation, Inc., https://en.wikipedia.org/wiki/Category:Classification_algorithms, (5 pages).

*Primary Examiner* — Dixomara Vargas
(74) *Attorney, Agent, or Firm* — BUCHANAN INGERSOLL & ROONEY PC

(57) ABSTRACT

A method for separately acquiring and outputting diagnostic nuclear magnetic resonance images based on water and fat derived signals, which method provides that the separation of the signal components corresponding to the intensity of the resulting pixels or voxels derived from the water of tissues in the body under examination from those signal components derived from the fat tissues in said body under examination of the step is performed by means of a machine learning algorithm, or with automatic learning and which algorithms are configured to classify the signal component as derived from water or fat tissues in the body under examination.

18 Claims, 8 Drawing Sheets

(51) Int. Cl.
*G06T 7/00* (2017.01)
*G06N 3/08* (2023.01)

(52) U.S. Cl.
CPC ...... *G06N 3/08* (2013.01); *G06T 2207/10088* (2013.01); *G06T 2207/20081* (2013.01)

(56) References Cited

U.S. PATENT DOCUMENTS

| | | | |
|---|---|---|---|
| 7,711,662 | B2 | 5/2010 | Buscema |
| 8,248,070 | B1* | 8/2012 | Wheaton ............ G01R 33/4828 324/307 |
| 2005/0165296 | A1* | 7/2005 | Ma .................. G01R 33/56563 600/410 |
| 2005/0260331 | A1* | 11/2005 | Wang .................... H01F 1/0063 427/2.1 |
| 2007/0233624 | A1 | 10/2007 | Buscema |
| 2011/0091090 | A1* | 4/2011 | Dahlqvist Leinhard ................ G01R 33/56527 324/309 |
| 2011/0268332 | A1* | 11/2011 | Hofstetter .......... G01R 33/4828 382/131 |
| 2012/0176131 | A1* | 7/2012 | Madhuranthakam ...................... G01R 33/4828 324/307 |
| 2013/0088226 | A1* | 4/2013 | Miyazaki ........... G01R 33/5607 324/309 |
| 2014/0062474 | A1* | 3/2014 | Zhou .................. G01R 33/5607 324/309 |
| 2015/0061672 | A1* | 3/2015 | Kannengiesser .. G01R 33/4828 324/309 |
| 2017/0131374 | A1* | 5/2017 | Choi .................. G01R 33/4828 |
| 2017/0307699 | A1* | 10/2017 | Rodgers ........... G01R 33/56527 |
| 2017/0350951 | A1* | 12/2017 | Samsonov ......... G01R 33/4828 |
| 2018/0315188 | A1* | 11/2018 | Tegzes ...................... G06T 7/11 |
| 2019/0310335 | A1* | 10/2019 | Nickel ............... G01R 33/5608 |
| 2020/0241099 | A1* | 7/2020 | Zheng ............... G01R 33/4828 |
| 2020/0278406 | A1* | 9/2020 | Sharma ............. G01R 33/4828 |
| 2022/0071490 | A1* | 3/2022 | Vaughan, Jr. ........ A61B 5/0042 |

FOREIGN PATENT DOCUMENTS

| | | |
|---|---|---|
| WO | 03077182 A1 | 9/2003 |
| WO | 2004063831 A2 | 7/2004 |

* cited by examiner

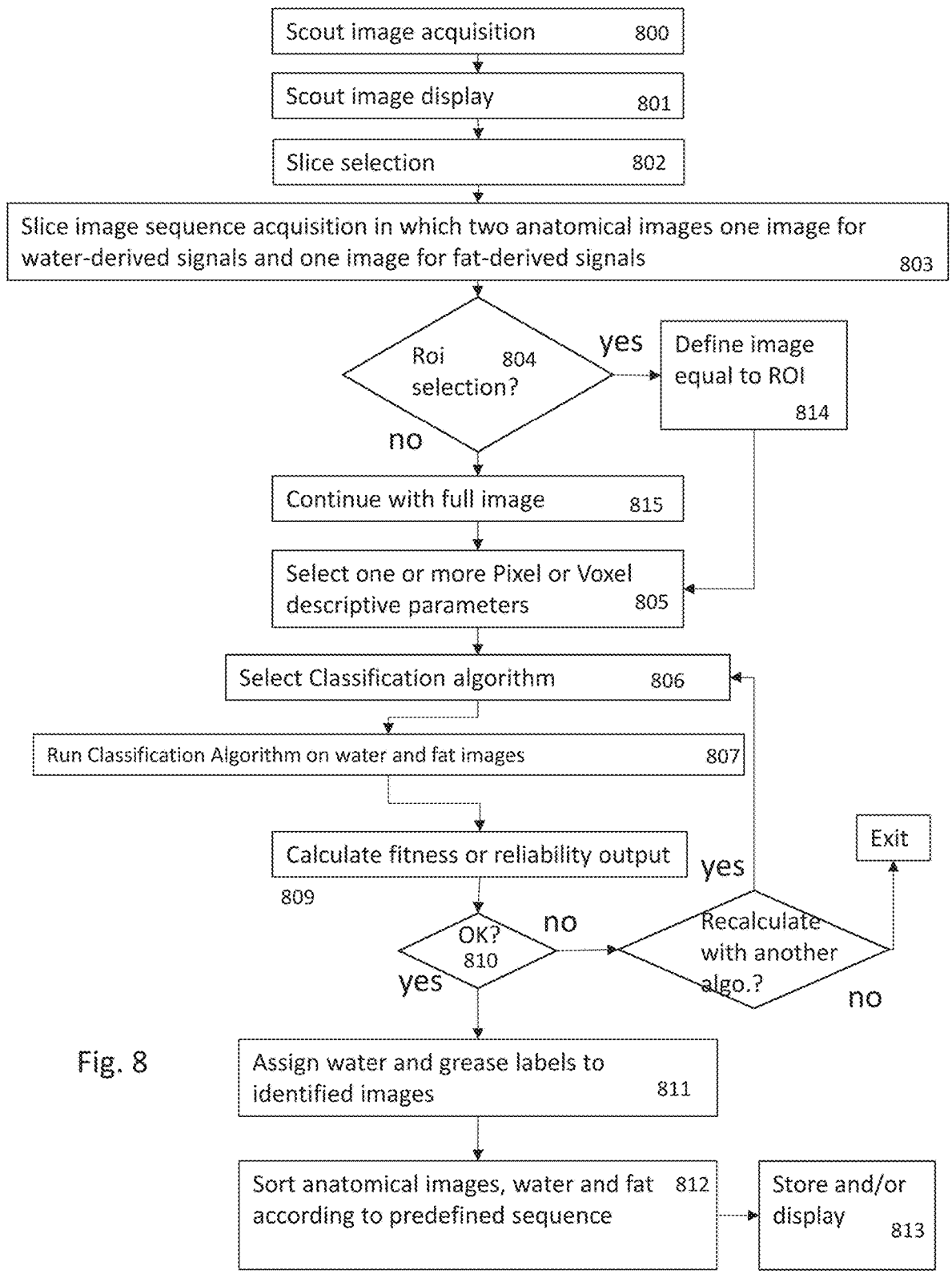

SYSTEM AND METHOD FOR FAT AND WATER DIAGNOSTIC IMAGING

TECHNICAL FIELD

The present invention relates to a system and a method for diagnostic imaging of water and fat.

BACKGROUND OF THE INVENTION

In general, diagnostic applications of magnetic resonance imaging (MRI) detect the signal of protons, which make up more than 90% of the nuclei in the human body. The protons detected are partly those related to water in tissues or are those contained in molecules such as proteins or carbohydrates or are those contained in the matter of which fatty tissues are composed. The signal intensities in the voxels of 3D images or the pixels of 2D images are derived from a combination of the spin density, and the longitudinal and transverse relaxation times (T1 and T2, respectively), as well as the parameters defining the imaging sequences used during the excitation and acquisition process of the MRI signals. By exploiting the special characteristics of hydrogen atoms, MRI can provide excellent contrast between soft tissues, depending on whether they are bound to water or lipid molecules. With a relatively short T1 relaxation time, the signal from fat often appears very intense in many important diagnostic imaging sequences and may obscure, i.e. not make visible by glare, the underlying pathology such as pulmonary oedema, inflammation, or increased tumour tissue.

For this reason, most MRI diagnostic imaging protocols use methods of suppressing fat-derived nuclear magnetic resonance signals to improve visualisation of such pathologies. This is particularly true for standard imaging sequences such as Fast Spin Echo (FSE), spoiled gradient echo (SPGR) and steady state free precession (SSFP). Reliable suppression of fat-derived nuclear magnetic resonance signals has the additional advantage of eliminating chemical shift artefact, by virtue of the fact that the fat-derived signal is no longer present and lower bandwidths can be used in combination with techniques to improve the signal-to-noise ratio (SNR) under conditions of fat-derived signal suppression.

On the other hand, however, there are a number of pathologies wherein direct visualisation of MRI signals arising from the matter of which fat tissues are composed may be desirable, such as fat tumours, adrenal adenomas, angiomyolipomas, liposarcomas and other mesenchymal tumours. In addition to this, there is also a strong interest in quantifying the amount of visceral adipose tissue as well as fat infiltrative diseases such as hepatic steatosis.

In order to be able to detect by means of diagnostic nuclear magnetic resonance imaging both pathologies that are optimally visible in images using resonance signals from water and pathologies that are optimally visible in images obtained from nuclear magnetic resonance signals from fat tissue, so-called separation techniques of water-derived and fat-derived nuclear magnetic resonance images are currently known. These known techniques make it possible to generate diagnostic images based on water-derived and/or fat-derived signals alone.

At the state of art, water-fat image separation methods are known which are based on chemical shift and are known generically as "Dixon" methods. In contrast to methods that suppress the signal from lipid tissue or selectively excite resonance echoes from water, methods known as "Dixon" methods rely on phase shifts created by differences in the resonance frequency of fat and water to separate nuclear magnetic resonance signals from water and lipid tissue. Phase information is encoded by acquiring images with slightly different echo times (TE) using the difference in resonance frequency between water and fat. By acquiring images with specific TE values appropriately selected, the combined signal from a voxel containing both water and fat signals can be decomposed into separate images generated on the basis of water-only signals and fat-only signals wherein fat-only signal images and water-only signal images are suppressed, respectively.

This type of approach, also called the "two-point" method, is however sensitive to inhomogeneities in the static magnetic field $B0$. These inhomogeneities lead to exchanges of images from water with those from fat and vice versa. This occurs because the inhomogeneities of the $B0$ static field create a natural ambiguity when only one chemical species (water, fat) dominates the signal from a pixel or voxel: in this case, the signal from fat is indistinguishable from the signal from water, which is offset from the resonant frequency of 210 Hz. Therefore, in order to have a reliable and correct separation of the water and fat images in the known methods, it is necessary to resolve these ambiguities by processing the image data with unwrapping algorithms.

At the state of art, modified and more complex methods known as "three-point" or "four-point" methods, such as those known from Glover and Schneider wherein a third image is acquired and used to compensate for inhomogeneities and thus prevent the exchange of water- and fat-derived images or vice versa, are now known.

These known methods have proved to have several drawbacks, the most serious of which is that they significantly lengthen the scanning time, i.e. the duration of a target scan. In order to reduce the penalty of Dixon methods in relation to scanning time, methods have been developed that comprise partial space acquisition k parallel imaging methods and multi-echo acquisition methods that are performed in combination with the aforementioned water/fat image separation methods. However, these technologies do not affect a reduction in time due to the separation of water and fat signals, but constitute artifices for shortening other steps in the nuclear magnetic resonance image acquisition process and thus circumvent but do not fully and satisfactorily resolve the above described drawbacks with respect to the water/fat image separation methods, both with respect to the reliability of the water/fat image separation and with respect to the scanning and/or image processing times.

Currently, there is therefore a need for reliable water/fat image separation techniques that do not significantly affect scanning and/or processing times without the need for other collateral artifices to shorten image acquisition times and without affecting image quality such as the signal-to-noise ratio.

Brief Description of the Invention

It is an object of the present invention to provide a method and system for diagnostic nuclear magnetic resonance imaging that allows the separation of water-derived and fat-derived images by eliminating errors due to static magnetic field inhomogeneities.

In its most general embodiment, the invention relates to a method for separate acquisition and output of diagnostic nuclear magnetic resonance images based on water-derived and fat-derived signals, wherein the method comprises the following steps:

(a) defining at least one image slice traversing with a predetermined relative orientation a body or a zone of a body under examination;

b) for at least said one slice, or for at least part or all of said slices when there are more than one, acquiring at least one anatomical image in nuclear magnetic resonance along said slice;

(c) for at least said one slice, or for at least part or all of said slices where there is more than one slice, and for each pixel or voxel of the nuclear magnetic resonance image acquired along said slice, perform a separation of the signal components corresponding to the intensity of said pixel or voxel arising from the water of the tissues in said body under examination from those signal components arising from the fatty tissues in said body under examination;

(d) for at least said one slice, or for at least part or all of said slices, when these are more than one, generating an image named water only which is generated on the basis of the signal components of the MRI signals derived from water only separated in the previous step;

(e) for at least said one slice, or for at least part or all of said slices when there are more than one, generating an image termed fat only which is generated on the basis of the signal components of the MRI signals derived from fat only separated in the previous step;

(f) Ordering the individual slice images in a sequence whereby, for each slice, said anatomical image(s) is (are) first, followed by said water-only image(s), followed by said fat-only image(s);

(g) Ordering the single-slice images in the order of slice position when there is more than one slice, wherein h) the separation of the signal components corresponding to the intensity of said pixel or voxel deriving from the water of the tissues in said body under examination from those signal components deriving from the fatty tissues in said body under examination of step c) being performed by means of a machine learning algorithm, which algorithms are configured for classifying the signal component as deriving from the water or fatty tissues in said body under examination.

The term 'machine learning' refers to the use of general mathematical and statistical algorithms which, when exposed to a given set of data in an initial 'training' phase (training and testing) and through a second phase of evaluation of the results with optimisation of the parameters, autonomously derive the function—not always known and not always knowable—able to identify in a different set of data (execution data), the most probable value of a condition defined by a parameter that presents expected values within a pre-established scale of values or a set of values, possibly indicating a degree of confidence in the estimate.

For the execution of the said method, it is possible to envisage different executive variants and different refinements which will be listed below and which can be used alternatively or in any combination or sub-combination among them. The combinations or sub-combinations explicitly described below are merely preferred examples which do not limit the general concept or the possibility of permutation of the individual variants or refinements in the various possible combinations even if not explicitly described.

In relation to the definition of the machine learning algorithm used for separation as in (h) above, this is configured by training and testing processes with image data from a database wherein the image data is uniquely correlated to the known outcome of belonging to signals derived from water and fat, i.e. generating nuclear magnetic resonance images relating to water or fat.

In addition, machine learning algorithms have feedback mechanisms related to the results of the processing they perform which, based on fitness parameters of the results or other statistical parameters of reliability of the results, determine an upgrade of the setting parameters of the results, such as different coefficients and/or the matrix of the weights of the individual nodes in the neural networks.

Classification algorithms are known state of the art and relate to solving a classification problem, i.e., a supervised learning problem that requires making a choice between two or more classes to be assigned to data, typically providing a probability for each class.

Non-limiting examples of classification algorithms that can be used individually or in combination are neural networks and deep learning algorithms, as well as more common algorithms such as the Naive Bayes Classifier, Decision Tree, Logistic Regression, K-Nearest Neighbours (K-NN) and Support Vector Machine (SVM). Combinations of classification algorithms can also be used, such as those known as Random Forest and other enhancement methods such as AdaBoost and XGBoost.

A more comprehensive example list of classification algorithms that can be used to perform the step of separating image data acquired by nuclear magnetic resonance into image data relating to signals derived from water and image data relating to signals derived from fatty tissues can be found at the following link https://en.wikipedia.org/wiki/Category:Classification_algorithms Further algorithms consisting of specialised neural networks in relation to image processing, such as the method described in US2007233624. In this case the algorithm acts in a different way from what happens with traditional neural networks wherein the matrix of the weights relative to the various nodes is modified to bring the internal functions of activation of the nodes to combine in such a way as to satisfy the boundary conditions defined by the parameters of the input and output variables that are determined by fixed values of the known cases in training, for which once trained, the network supplies output parameters when input parameters are introduced which output parameters are determined by the matrix of the weights and by the parameters of the functions of activation of the nodes that have been determined in the training phase. In fact, in this algorithm the network is structured foreseeing a node for each pixel or voxel of the image and putting as output the values of the matrices of the weights of the single nodes, which in turn modify the characteristics of the various pixels or voxels.

It is possible to envisage different ways of defining descriptive parameters of the appearance of a pixel or voxel that are a function of whether an MRI signal comes from water or fatty tissue.

One embodiment provides that as a parameter of the pixel or voxel the intensity of the pixel or voxel is used.

Preferably, this intensity is expressed on a grey scale, whereby brighter shades of grey correspond to greater intensity and darker shades of grey correspond to lower intensity.

An alternative embodiment may provide that a pixel or voxel is always connoted, with regard to the identification of the origin from water or fat of the corresponding signal in nuclear magnetic resonance, by an intensity value, also possibly expressed with a grey scale, but within the processing of the algorithm, each pixel or each voxel is identified also by the intensity values of the pixels or voxels surrounding it and which are at least immediately adjacent to it, that is, so-called pixels or voxels of the gradient 1 surroundings.

The European patent EP1345154 describes a pixel or voxel coding system which provides for defining the characteristics of descriptive parameters of a pixel or voxel as a function of the value of said parameters of the pixel or voxel under consideration and also of the pixels which surround said pixel or voxel under consideration and are immediately adjacent thereto.

The accuracy and reliability of the results provided by a self-learning algorithm also depend above all on the quality of the known data based on which, the algorithm is trained and tested. Various effects can occur during training such as the presence of relative minima or maxima wherein the iterative process of calculation becomes entangled so that a certain variable no longer progresses towards a convergence condition, thus affecting the entire process of defining the internal parameters of the functions that the algorithm uses to perform the processing and which are defined during the training phase.

Therefore, an improved embodiment involves combining embodiment s according to one or more of the variants or combinations or sub-combinations described above with a system and in particular with an optimisation algorithm of the database of known training and testing cases.

Training and testing database optimisation systems are known, and an example may be the system described in European patent number EP1586076. The training and testing database optimisation algorithm exploit the combination with a neural network to generate alternative combinations of records in a plurality of child training and testing databases. The fitness of the result of a neural network trained with the different databases determines which of these alternative databases is retained as the parent database and which is discarded. The optimisation process is iterative and can be stopped either by reaching a predefined fitness value or by a predefined maximum number of iterations.

In the example described in this document, subgroups of data records in a training database containing known data are generated by combining different data records of the said database by selecting these records from those present in the database of known cases. Each database is used to train a neural network or a combination of neural networks and the quality of each of the said databases relative to a better or worse neural network is measured on the basis of the fitness or the reliability of the result furnished by each network trained with a different specific sub-group of records. A genetic algorithm is used to generate new combinations of data records for new training databases. These are used to re-train the networks and the fitness of the trained networks is calculated again. Each iteration is carried out starting from databases of records that have obtained the best results of fitness as parents for the calculation and the generation of a new daughter generation of databases of records and this is repeated until a value of fitness of the neural networks above a certain threshold limit is obtained or a maximum number of iterations is reached. The record database that provided the best fitness at the end of the succession of iterations is the optimised training database.

According to a further embodiment of the above-described method, after the step of acquiring a first MRI image along a predetermined slice, and prior to the step of separation the steps of for at least said one slice or for at least part or all said slices, when these are more than one, acquiring an image named water only which is generated on the basis of MRI signals derived from water only;

for at least said one slice or for at least part or all said slices, when these are more than one, acquiring an image named fat only which is generated on the basis of MRI signals derived from fat only;

while a validation step is envisaged wherein the machine learning algorithm is configured and used for the validation classification of the acquired images as relating only to the signal component deriving from water or relating only to the signal component deriving from the fat tissues present in the body under examination.

According to this further embodiment of the present invention, said steps of acquiring the water-only image(s) and the fat-only image(s) are subjected to a further validation step comprising analysing the probability that said images actually derive from water-only MRI signals or fat-only MRI signals and which step comprises processing said images with a predictive algorithm, such as a classification algorithm or the like, which algorithm has been trained and tested on the basis of a plurality of MRI images of which it is known and confirmed that they are images generated on the basis of signals derived from only water and only fat.

Similarly, to the first embodiment, once the images relative to water and fat have been generated, the steps of ordering the images relative to the single slices in a sequence that for each slice envisages firstly the said anatomical image or images and then the said water-only image or images followed by the said fat-only image or images;

ordering the images relative to the single slices according to the order of position of said slices when there are more than one of them.

According to an embodiment of the method according to the present invention, the method comprises performing a sequence of acquiring water and fat images comprising acquiring a succession of two anatomical MRI images and subsequently acquiring two images whose signals are related to water and one image wherein said signals are related to fat, said images being sorted according to a sequence comprising first said two anatomical images and subsequently said water-related image and said fat-related image, said sequence being kept fixed for all MRI image acquisitions, while the said machine learning algorithm, i.e. the said predictive or classification algorithm is used to identify which of the two images acquired subsequently to the two anatomical images is relative to water and which is relative to fat and to generate the said sequence of images.

According still to an embodiment of the method of the present invention, there is provided a step of reducing the size of the image, i.e. the number of pixels or voxels. This reduction step precedes the step of processing the parameters describing the appearance of the pixels or voxels, for example the intensity expressed in a grey scale.

An embodiment foresees to use an operator of analysis of the parameters determining the aspect of the pixels, which operator identifies regions of the image to be analysed wherein the parameters of definition of the aspect of the pixels are relative to signals deriving from water or from fat, submitting to the process of elaboration by means of the algorithm of machine learning only the pixels that fall within the range of said parameters of aspect that are functional to the determination of the image as deriving from water or from fat.

Such an operator may be a filter or the like in the form of a "travelling window" having a predetermined pixel size, i.e.

having a size covering or overlapping a predetermined number of pixels, for example nine pixels of which the central pixel is the target pixel.

An alternative embodiment of the aforementioned step of reducing the number of pixels may provide, for example, for merging together into one or more pixels or voxels the pixels or voxels of the original image having the same intensity, for example with reference to the metric measured according to said grayscale.

According to one embodiment, the determination of the identity condition is performed by providing a field of the intensity value measured with said grayscale which is centred on a predetermined intensity value.

According to a first embodiment, the maximum value and the minimum value of each intensity value field defining the intensity values of the pixels or voxels to be considered identical and therefore to be merged together may be defined in a fixed way. In this case, wanting to define a priori an image size, i.e. an image formed by a pre-established number of pixels or voxels, for example and generally an image formed by 4096 (64×64) pixels or by or 65536 (64×64×16) voxels, so as to always generate an image with fixed and pre-established dimensions to be submitted to the processing by means of the classification algorithm, the phase of reduction of the image size foresees to merge the pixels or voxels having an intensity falling within one of the intensity fields foreseen in more than one pixel or voxel according to the fixed condition at the boundary that the final image must present the size, that is the number of pixels or voxels established at the beginning, for example 4096 pixels for a 2D image along a slice or 65536 for a 3D image of a target region under examination.

In an embodiment, said maximum value and said minimum value of the intensity field, may be dynamic, whereby the resolution of the greyscale as a metric for measuring the intensities of the pixels or voxels becomes greater or lesser as a function of the number of pixels or voxels resulting to have an intensity falling within one of the intensity value fields and the boundary condition defining a final size of the image to be processed relative to the number of pixels or voxels.

A third executive variant may instead comprise performing the image size reduction step without defining a reduced image having a predetermined fixed number of pixels or voxels and adjusting the processing algorithm to the final image size in relation to, for example, the number of inputs of a neural network or other parameters that depend specifically on the type of classification algorithm used.

In an embodiment, when the processing time allows it, it is possible to modify also the resolution of the grey scale in relation to the fields of values which define which values of intensity of the pixels or of the voxels are to be considered identical among them, or the maximum and minimum value of intensity of the said fields of values, in function of the fitness of the result or other statistical parameter of measurement of the reliability of the result.

Always when the times of elaboration would not be increased to an extent not acceptable from the practical point of view, a possible can foresee to combine the elaboration of the images with an algorithm of classification for the separation of the images deriving from water from those deriving from fat, with an algorithm re-entering in the classification of algorithm of machine learning or self-learning, which optimises the subdivision of the greyscale with reference to fields of intensity or greyscale values for which pixels or voxels are to be considered identical or to be merged into a single pixel or voxel or into a group of a predetermined number of pixels or voxels for the reduction of the size of the image to be processed with respect to the originally acquired image.

An example of a possible algorithm for optimising the field subdivision of the greyscale constituting the pixel or voxel intensity metric may be a genetic algorithm. This generates new subdivisions in fields of values of the grey gradation scale, relative to the definition of the limit values of these fields by combining according to genetic rules the subdivisions of the grey gradation scale previously defined and according to the parameters of fitness or reliability of the classification result obtained by the classification algorithm for the images reduced in size with the said previous subdivisions in fields of values of the grey gradation scale.

Subdivisions of the greyscale that provide reliability or fitness results below a certain threshold are discarded, while the others are combined according to combination rules typical of genetics and reproduced in mathematical combination functions in the genetic algorithm.

In this way, the genetic algorithm converges towards an optimal metric of determining the ranges of values for which pixels or voxels must be fused together to generate an image of reduced size which, however, maintains constant or even improves the reliability of the classification of the original images into images derived from water or fat.

According to an embodiment, the images acquired according to one or more of the preceding claims are subjected to an intensity rescaling step in relation to a single identical grey scale, i.e. a single pixel or voxel intensity metric.

With reference to the various variants set forth above, these are to be considered as non-limiting examples of the more general concepts that allow the technician in the branch to implement the described forms of execution both in general form and in specific form by applying only the basic technical knowledge typical of the expert in the branch.

The present invention also relates to an MRI system for generating images acquired by means of nuclear magnetic resonance separated with respect to signal contributions generated by water and fat, which system is configured to implement the method according to one or more of the variant implementations described above.

BRIEF DESCRIPTION OF THE DRAWINGS

These and other features and advantages of the present invention will become clearer from the following description of some example implementations illustrated in the accompanying drawings wherein:

FIG. 8 illustrates a flowchart according to a further embodiment of the present invention.

FIG. 1 shows a flow chart of a first executive example of the water/fat image separation method according to the present invention.

Figure 1:
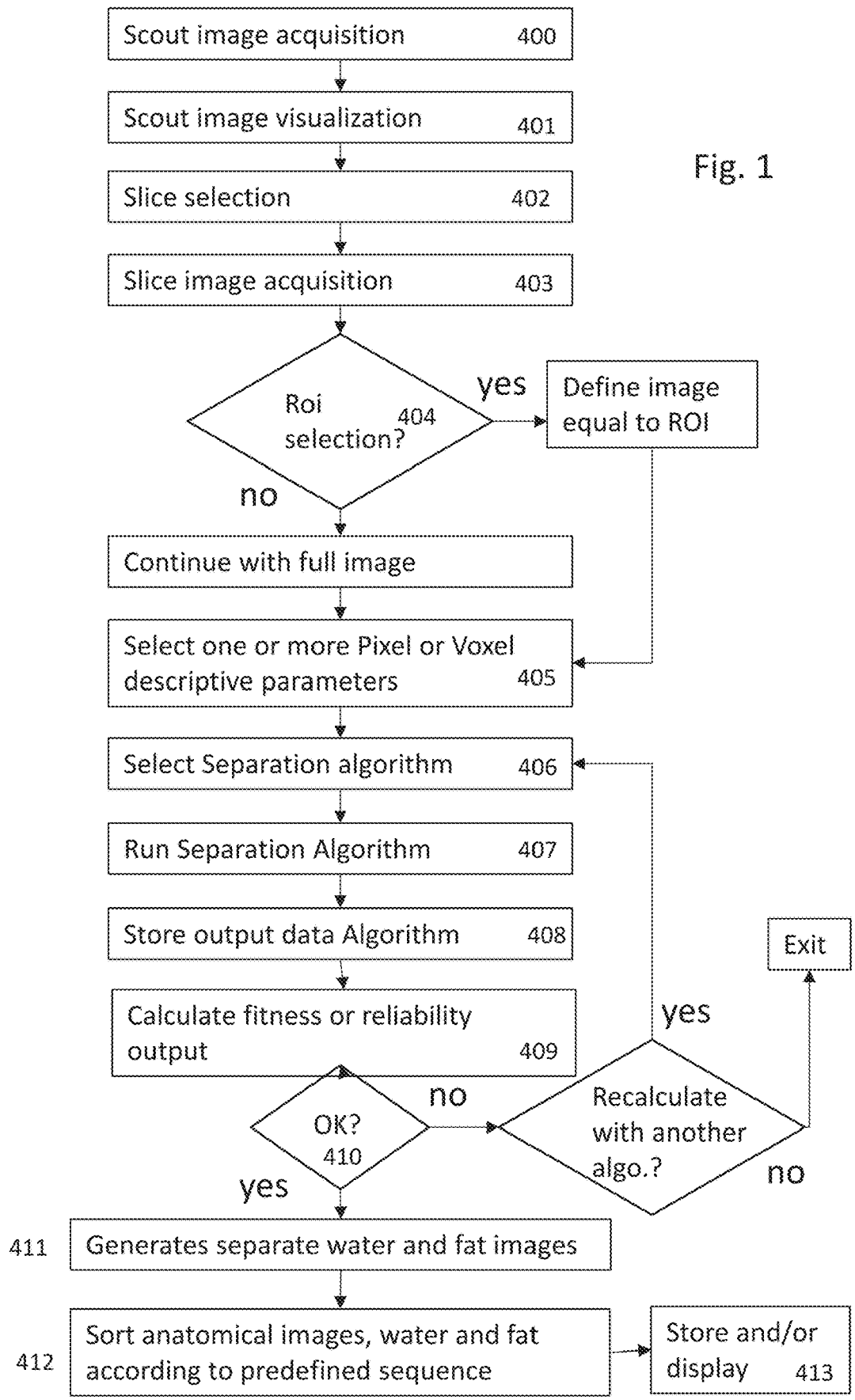
FIG. 1 shows a flowchart of the method according to the present invention relating to the separation of MRI images derived from water from MRI images derived from fat.

At step 400, a scout image of a target is acquired, as is typically the case for MRI image acquisition. The purpose of this scout image is to select one or more planes section along which an image is to be acquired. On the displayed image 401 at least one section plane and/or slice along which an image 402, 403 is to be acquired is defined.

In step 404, a specific region of interest ROI can be selected, which is an area of the entire acquired image centred on an anatomical detail of interest.

The selection of an ROI allows to limit the size of the image and thus reduce the data on which the processing will be performed thus reducing the computational load and processing time.

In step 405, descriptive parameters of the appearance of the pixels or voxels are selected which are relevant for the purpose of separating the water and fat images and which in this case are in particular the intensity of the resonance signal relative to the area corresponding to each pixel or voxel.

As will appear more clearly below the intensity of the signal is expressed in the pixel or voxel with a metric defined by a grayscale that makes the appearance of the pixel lighter or white for higher values of signal intensity and progressively darker and darker grey tones until black for progressively lower values of intensity.

At step 406 a separation algorithm is selected which as described above is a machine learning algorithm. Among the different algorithms of machine learning for the solution of the problem of separation of the images derived from water or fat, it is preferable a so-called algorithm of classification or clustering that attributes the patterns of input data of the algorithm to one or more classes or groups or categories defined a priori and that characterise the output of the algorithm.

The separation algorithm is then launched by being given as input the intensity values of the pixels or voxels forming the selected image and/or ROI selected in the previous steps as set out in step 407.

The algorithm classifies the contributions of the various pixels as deriving from water and/or fat and thus allows the reconstruction of images deriving from water only and fat only.

According to a preferred embodiment, as is well known in the state of the art, on the basis of the chemical shift between water-derived and fat-related resonance frequencies, it is possible to optimise the image acquisition sequences to generate water-derived and fat-only images. In this case, however, the separation resulting from the acquisition sequences can lead to errors due to both small and small inhomogeneities of the static magnetic field, whereby the acquired images can be interchanged.

Therefore, according to a further feature of the invention, the process of separating images derived from water and fat can be improved by performing the acquisition of two images with two alternative sequences one set specifically for acquiring images derived from water and the other set specifically for images derived from fat.

Subsequently the method foresees to execute the elaboration step with the algorithm of classification on both the images and therefore to validate the attribution of the acquired images to the contributions of signal deriving from the water only and to those deriving from the fat only, avoiding to a very large extent eventual exchanges of images relative to the provenance from water or from fat without however necessitating further acquisitions of validation images as foreseen in the known methods.

The results of the separation algorithm are stored as indicated in step 408 and a statistical fitness value of the attribution of the acquired and processed images is calculated, step 409.

This step is usually performed in processing by machine learning algorithms, since the result obtained from any execution of the algorithm is part of a verification and learning process of the same, and measuring the fitness of a processing cycle allows the intended self-learning processes to evaluate the result and use it or not as usable information for an adjustment of the configuration of the algorithm itself.

If the fitness value, i.e. the reliability of the result, is below a certain predetermined threshold, it is possible to repeat the separation, for example by modifying certain algorithm execution parameters or changing the type of algorithm or by using an algorithm trained with training methods and/or a modified training database.

If the reliability is sufficient at the decision step 410, it can proceed to the step 411 of generating images derived from water and fat.

As indicated in step 412, the images are then sorted into a sequence corresponding to the acquisition sequence. And then at step 413 stored for future reference and/or further processing and/or the images are displayed.

As already highlighted in the introductory part, in order to have high performance of machine learning algorithms such as the classification algorithms considered herein in particular, it is necessary to optimise the training of these algorithms. The fitness of the results, that is their reliability depends also on how the parameters that identify and describe the characteristics of the pixel or voxel of an image are encoded, when the parameter or parameters to be evaluated are those relative to the aspect that the pixel or voxel assumes in an image.

The flow chart considers the use of an already trained algorithm. However, it is worth pointing out in this context that for the training phase there are various state of the art algorithms of optimisation of the database of known cases necessary for the training of the algorithm, that is to give the algorithm an initial basic knowledge which will then be increased on the basis of the execution of the same on the cases to be processed.

Among the various methods of generating a database of known cases present in the state of the art, an example is the optimisation method described in the European patent EP1586076. According to this method, from a database of known cases, i.e. cases wherein the attribution of an image to signal contributions from water or signal contributions from fat is certain and validated according to known techniques, a predetermined number of records are selected randomly. A predetermined number of these random databases are generated, each of which is used to train the same type of machine learning algorithm. Each trained algorithm is then tested with a different composition of the training database and the fitness for each algorithm is calculated.

This set of algorithms constitutes the starting population of a genetic algorithm and the gene of each individual is the specific training database. The value of the fitness of each algorithm constitutes the criterion of selection of each individual of the initial population to generate a population of parent individuals from which to proceed to the generation of a population of offspring individuals with the known mechanisms of cross over and of mutation that foresee the combination of the genes of the parent individuals for the generation of the genes of the offspring individuals. Generally, these mechanisms cause the records of the training database of the two parent individuals to be combined, generating a new training database. The child algorithms are constituted by the algorithms trained on these new training databases and whose fitness is also calculated. The cycle ends with the election as population of parent individuals for a new cycle of the parent individuals and of the child individuals of the first cycle that have obtained a fitness that, for example, is better than a certain minimum value. The others are discarded.

The cycles are repeated until the reaching of a maximum pre-set number of iterations or until the reaching of a fitness value superior to a certain threshold or until the reaching of a condition wherein for two or more successive executions the fitness of the child individuals remains substantially unchanged.

The above is only an example of optimisation of the training database. It is possible to foresee alternatively or in combination other methods of optimisation of the training database which can also be based on methods of filtering or of classification of the records which form the training database.

Regarding the definition of the parameters that constitute the input values of the algorithm that are typically genetic, the document EP1345154 describes a system of coding of pixels or voxels that foresees to define the characteristics of descriptive parameters of a pixel or voxel in function of the value of said parameters of the pixel or voxel under examination and also of the pixels that surround the said pixel or voxel under examination and are immediately adjacent to the same. This methodology of encoding allows to avoid isolating a pixel from its context making the result of the elaboration more reliable.

FIG. 8 shows a flow chart of an alternative embodiment of the method according to the present invention.

In this case, the method comprises an image acquisition sequence, i.e. an image acquisition sequence not to be confused with the acquisition sequences concerning encoding and excitation of resonance signals, which image sequence is typically used in the state of the art and wherein for a slice or for each slice two anatomical images are acquired in succession and after these respectively an image relating to NMR signals deriving from water and an image relating to NMR signals deriving from fat.

For these last two images it is possible to foresee the use of acquisition sequences that are calibrated respectively for the optimisation of the acquisition of signals coming from water and/or fat or for the suppression of signals coming from fat.

The process begins with acquiring a scout image as indicated in step 800 and displaying the same in step 801. On this scout image, the user can select one or more slices along which to perform the actual acquisition of the NMR images, that is, of the resonance signals from which to reconstruct the NMR image relative to the selected slice as indicated in step 802. Step 803 provides for the acquisition of the succession of images (sequence of acquisition of the four images of which two anatomical images one relative to water and the last relative to fat). As indicated in step 804, in order to limit the data to be subjected to processing and therefore optimise both the result of the classification and at the same time reduce the computational burden by reducing the number of pixels to be processed, it is possible to select an ROI, that is, to select one or more regions of the image to be processed whose pixels are representative for classification as signals deriving from water or signals deriving from fat. This process is described in more detail below.

Once the choice of the ROI has been made, which for example may comprise only part of the acquired image or the entire image as indicated by way of non-limiting example in steps 814, 815, descriptive parameters of the image pixels or voxels are selected which are related to whether the signal represented with said pixel is related to water or fat as indicated in step 805.

Since several classification algorithms can be envisaged at step 806 the freedom is left to select a specific classification algorithm which may possibly also comprise a combination of classification algorithms and/or a classification algorithm with other types of algorithms.

At step 807 the selected algorithm is executed and at step 809 the fitness of the result is calculated if the fitness falls within a range of values for which the result is considered reliable or good, as indicated at step 810, one proceeds to step 811 wherein the label identified by the algorithm executed on the same or on part of the pixels thereof is attributed to the processed image and which label identifies said image as relating to water or fat.

Otherwise, it is possible to repeat the processing possibly modifying the algorithm and/or modifying alternatively or in combination the descriptive parameters of the pixels or voxels and/or the ROI.

Finally, in step 812, it is envisaged to perform the sorting of the images according to the predetermined sequence, that is, first the two anatomical images, then the image recognised and labelled as deriving from water and finally the image recognised and labelled as deriving from fat. This succession of images can be stored and/or displayed as indicated in step 813.

Since in both described embodiments, the acquisition of the MRI images already requires quite long scanning times, it is important to be able to keep the examination times short, so as already mentioned above an aim of the present invention is to reduce the examination times. In this case, it is possible to reduce the processing time by proceeding to a reduction in the number of pixels or voxels of an image.

Since the relevant parameter for determining the origin of the signal contribution from water or fat is the intensity value of the pixel or voxel which is expressed in the image according to a grey scale, it is possible to limit the number of pixels or voxels by grouping in a single pixel or in a group of pixels or voxels having a smaller number of pixels or voxels the pixels or voxels of the initial image which present an identical intensity, obviously within a tolerance range of the intensity value.

In order to perform this image size reduction, several alternatives can be followed. However, a maximum image size to be used can be defined and is typically 256 pixels considering a 2D image.

According to a first of the process of reducing the number of pixels to be subjected to processing for the classification and labelling of an image as a water- or fat-derived image, the reduction is performed by analysing one or more of the parameters that determine the appearance of the pixel or voxel for example the grey gradation values of the same or the intensity of the same when the intensity is represented in a grey gradation scale that determines the visual appearance of the individual pixels based on the intensity of the signal or combination of signals received relating to the corresponding pixel or voxel.

In an embodiment, it is possible to subject the image to be classified to a filtering or analysis procedure which identifies in said image only pixels or voxels whose grayscale gradation falls within a certain range of said grayscale or a combination of two or more ranges of said grayscale with which pixels are represented in the visual image.

There are several known methods of making these filters. One form of implementation involves, for example, a filter of the so-called travelling window type, wherein a window corresponding to a certain number of pixels is slid along the image and represents when combined with the pixels on which an operator performs an operation, for example selection or other operations. The combination of the operator may be, for example, an operation according to a pre-established function such as an addition, a subtraction, a multiplication, a division, a convolution, or other mathematical operations, for example, typical of matrix calculation.

The result is that at least a part of the pixels of the image to be processed is selected for processing with the classification algorithm, which part of pixels has values of the parameters describing the appearance of the pixels with values which are corresponding to those functional for the determination of whether the image is related to water or fat.

As a non-limiting example, pixels are selected from one or more regions of the image to be processed whose corresponding signal intensity value and thus whose grey gradation in the grey scale expressing said signal intensity falls within a certain signal intensity or grey gradation range.

According to an executive variant for determining the relevance or irrelevance of an image pixel for the water or fat classification of the image, it is also possible to provide an implementation form wherein, in addition to the parameter representing the appearance of the pixel i.e. the value of the signal intensity corresponding to said pixel, the relations of this parameter to the parameter values of the contour pixels are also considered.

This further executive form can also be implemented using an operator of the translatable window type which has an extension equal to, for example, nine pixels in the 2D form or 27 pixels in the 3D form and which operator includes functions for selecting the central target pixel as useful or not for the classification process which include combinations of the values of the descriptive parameters of the central target pixel and at least or all the contour pixels.

Typically according to one possible example the intensity values, i.e. the corresponding grey gradation of the contour pixels is used to calculate statistical weights of the corresponding value of the target pixel on the basis of differences, averages, standard variations or other similar functions which are based on the differences of said parameters between the target pixel and the contour pixel and the distance between the target pixel and the contour pixel.

A non-limiting example of this type of filtering for selecting individual pixels for use in the classification process is described, for example, in document WO03077182A1. In this document, a method for encoding a target pixel in an image is defined the characteristics of that pixel are also determined on the basis of the characteristics of the contour pixels directly adjacent to the target pixel.

Figure 2:
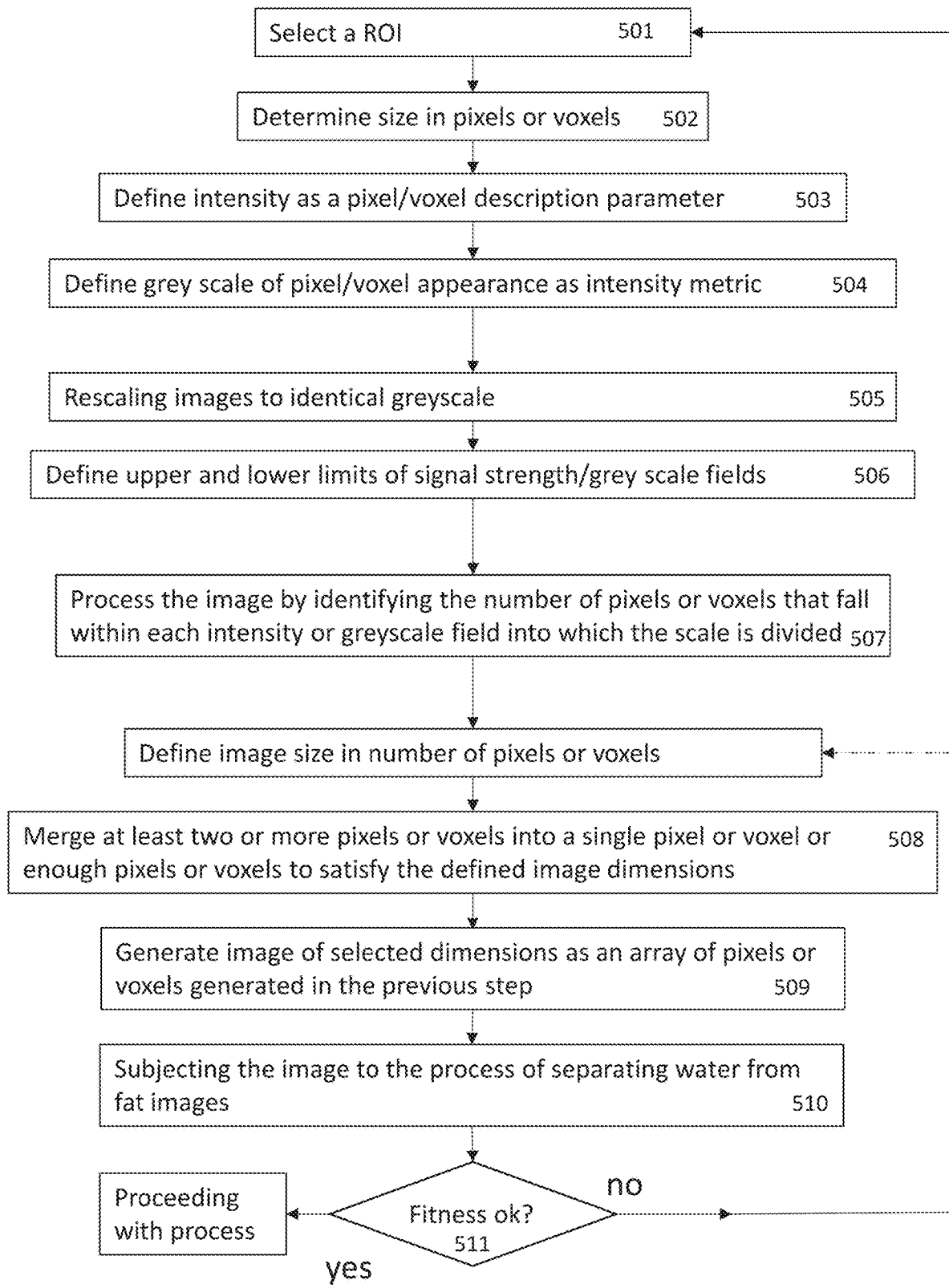
FIG. 2 is a flowchart relating to the step of determining the optimal image size to follow the algorithm for separating water-derived MRI images from fat-derived MRI images.

The flow chart of FIG. 2 shows a further of the process of reducing the size of the acquired images to be subjected to processing of separation of water and fat images.

It should be noted that this embodiment can be envisaged in combination with or alternatively to the one described above.

In step 501, an ROI is selected in the acquired image, which makes it possible to limit the processing from the outset to only an image area of interest. Step 501 can also be omitted, i.e. the entire image is processed.

In step 502, a desired image size is defined by indicating the relative number of pixels or voxels.

In step 503, their intensity is defined as a parameter for describing the characteristics of the pixels or voxels, and in step 504, a scale of grey gradations is defined which determine the appearance of the pixel or voxel in the image as a function of the corresponding intensity value. All images submitted for processing are heated so that the intensity values are within a predetermined range, for example 0 for 0 intensity and 1 for maximum intensity. This step denoted by 505 allows the grayscale metrics to be correlated with the intensity values, making all images comparable with each other.

In step 506 an upper limit and a lower limit of greyscale fields into which the greyscale is divided is defined.

In step 507 the pixels or voxels of the image are grouped according to the greyscale field to which they belong.

A range of possible image sizes is then defined considering the number of pixels in each group and the fact that these pixels can be merged together into a single pixel or into two or more pixels reducing the number of pixels that were initially classified as belonging to the same grey scale field. The process of combining or merging the said pixels is performed in step 508.

A new image is then generated which has a smaller number of pixels or voxels depending on the choices of the number of pixels wherein the pixels having a grey gradation falling in the same field have been merged with each other, step 509.

The new image is then subjected to processing with the separation algorithm as set forth in step 510 and the fitness of the result is calculated in step 511. If the value of the fitness is less than a certain minimum threshold, the process is repeated by reconsidering the number of pixels to be fused together and then modifying the size of the image always having as maximum size the one set in step 502. Steps 508 to 511 are then repeated.

If the fitness is better than a predetermined minimum threshold, the process continues as described with reference to the flowchart of FIG. 1 and as indicated by step 512.

The reduction of the image size may be performed according to various alternatives. In the example embodiment of FIG. 2, it is contemplated that a maximum image size is chosen, while the image reduction is in turn chosen on the basis of the number of pixels that can be fused together as they fall within the same grey gradation range into which the scale is divided. However, it is also possible that the choice of the size of the reduced image is fixed and therefore the number of pixels to be fused together that fall within the same grayscale field or the extent, i.e. the maximum and minimum limits of the fields into which the grayscale is divided, are modified.

Figure 3:
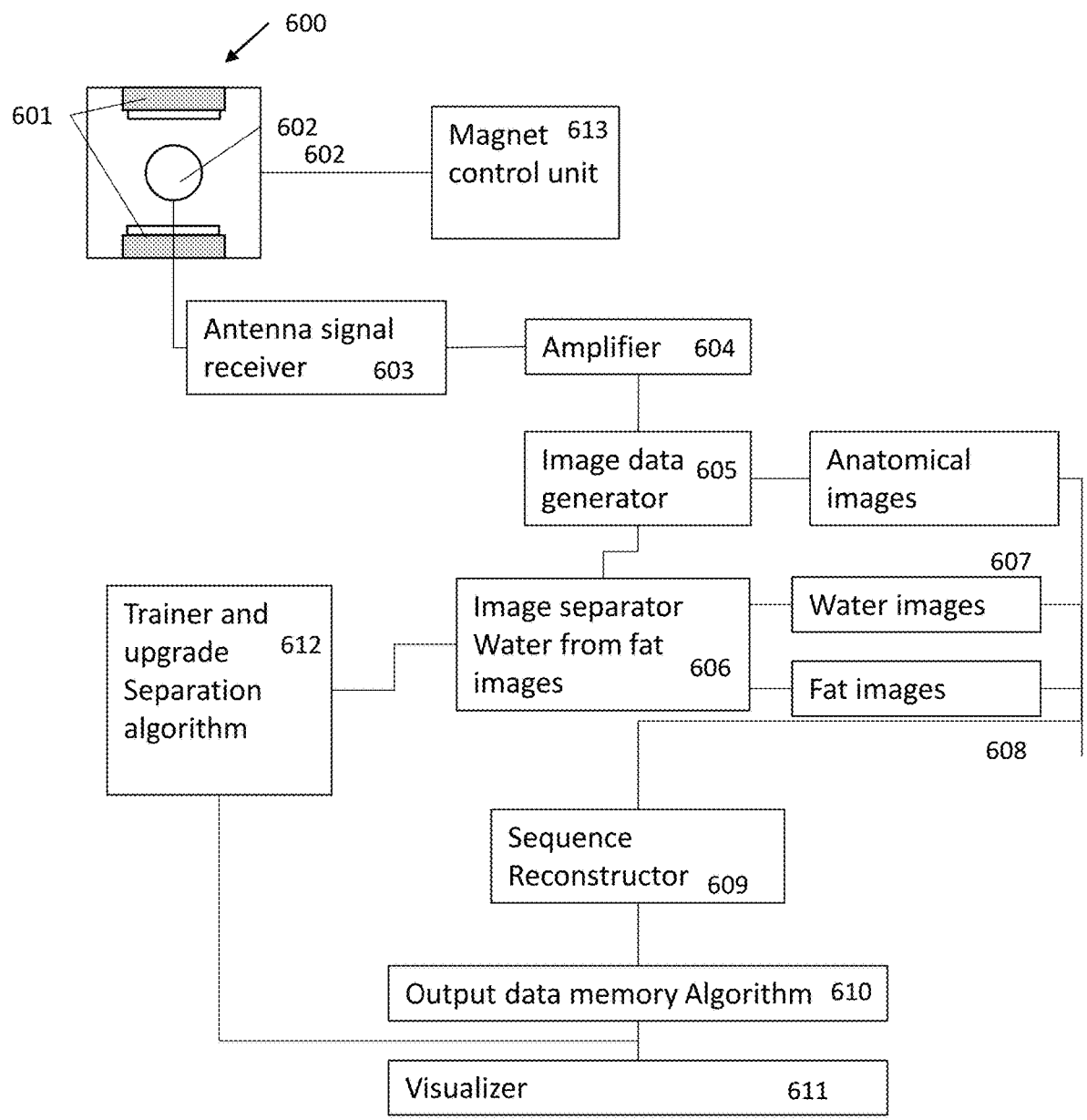
FIG. 3 is a block diagram of an MRI image processing unit for the separation of water- and fat-derived images.
Figure 5:
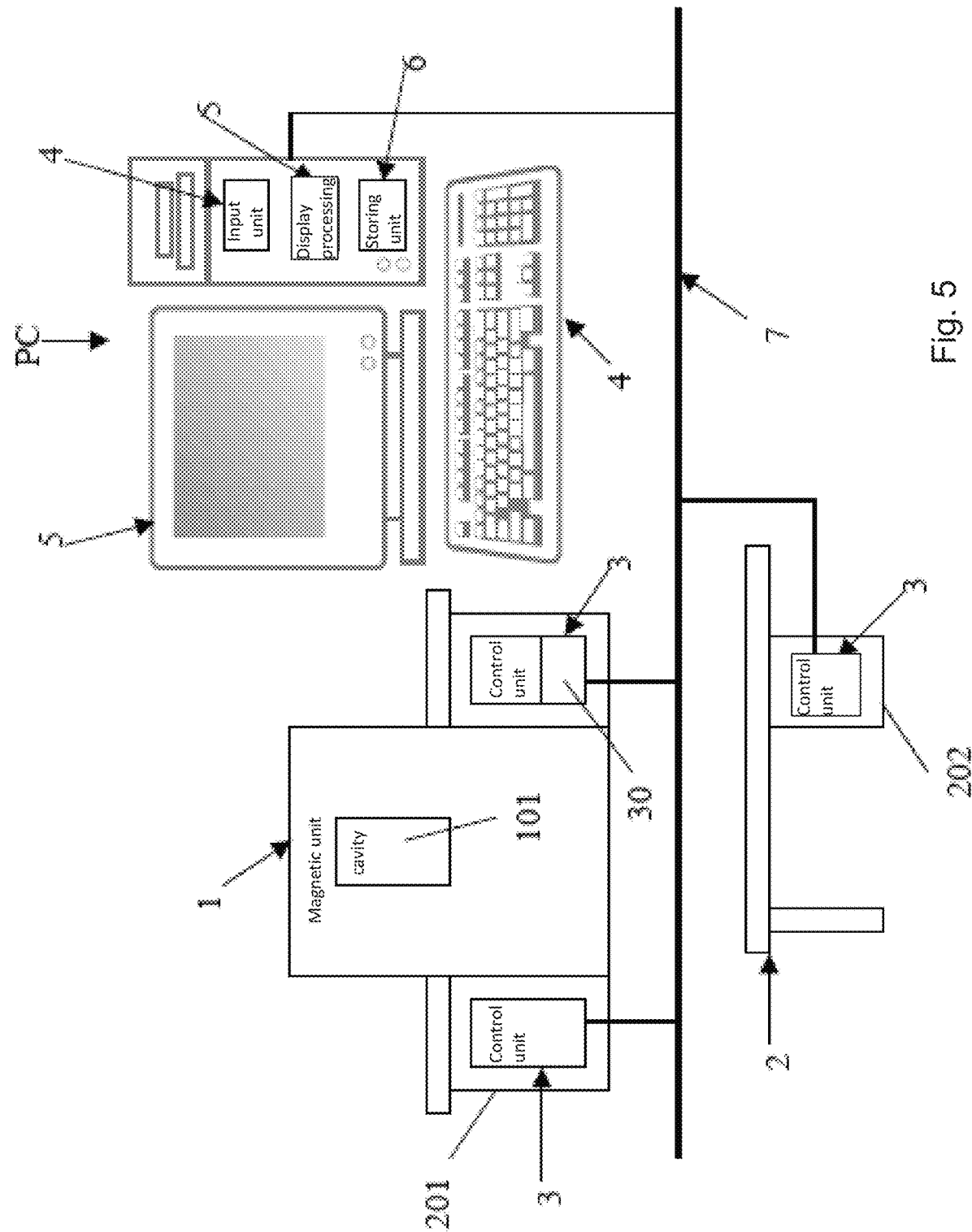
FIG. 5 schematically illustrates an example of a nuclear magnetic resonance imaging machine according to the invention.

With reference to the system for separating water and fat images, an example embodiment of a generic embodiment is shown in FIG. 3. In this embodiment, the system for separating water and fat images using the method of the present invention is integrated in an MRI apparatus. The magnet and other parts associated therewith are indicated globally by the icon 600. By 601 are indicated poles and by 602 an antenna for receiving resonance echoes. With block 613 are indicated all the usual control and setting systems of an MRI scanner, for example those indicated in greater detail in the s of FIGS. 5 to 7. The antenna signal received by a receiver 603 and subsequently amplified 604 is initiated to an image generation section 605. The illustrated embodiment includes an acquisition mode wherein an anatomical image is acquired for each slice and subsequently, with a dedicated and optimised acquisition sequence, an image relating only to water and an image relating only to fat. The anatomical image is memorised while the images acquired with the acquisition sequences optimised for water only and fat only are subjected to processing by means of the classification algorithm according to one or more of the previously described s. This processing takes place in a processing unit indicated by a water/fat image separator and the number 606. The result of the classification validates that an image belongs to the images derived from water only and to the images derived from fat only. These are stored in dedicated memories or memory areas 607 and 608 respectively.

A further processing unit 609 then sorts the images corresponding to an acquisition sequence which provides for the acquisition for each slice or ROI, first of the anatomical image, then of the image relating to the contributions of water only and then of the image relating to the contributions of fat only. The images thus ordered are then stored in a memory 610 and, if necessary, displayed in a display 611.

The display may be in a predetermined order and in succession, for example according to the sequence wherein they have been ordered, or the display may be simultaneously in several areas of a display screen side by side, or it may be based on recall or selection by the user.

When the algorithm is not of the self-learning type, the records used for processing and the result of the processing are used to be added to a database of known cases which corresponds to or from which a training database is generated, this operating unit being indicated by 612 in FIG. 3.

Figure 4:
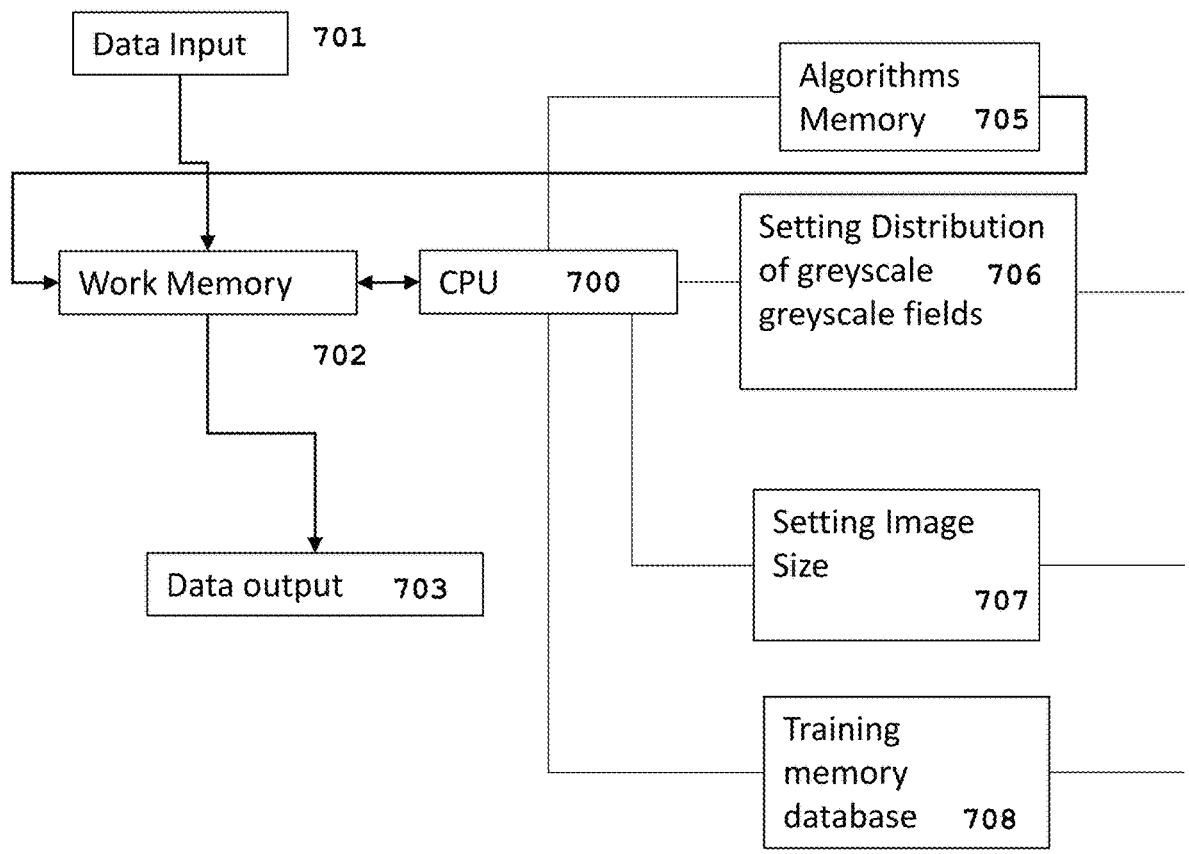
FIG. 4 shows the configuration of an of a processing unit for performing the method according to the present invention.

FIG. 4 shows a block diagram of an example implementation of a processing system that can be envisaged as a separate or separable unit, i.e. not permanently integrated into an MRI apparatus.

A CPU 700 controls the flow of data and peripheral units by executing peripheral control programs and processing programs which encode instructions to load input data perform algorithm processing steps and make output data available.

For this purpose, the processing system includes a data input interface denoted 701 that communicates with a working memory 702 and an output interface 703. The processor controls memories or memory arrays wherein are stored programs encoding instructions to execute one or more processing algorithms for water/fat image separation, processes for setting the distribution of greyscale fields into which the greyscale is divided, processes for rescaling the greyscale, processes for setting the size of the images, and a memory wherein a training database is stored.

These memories are indicated in FIG. 4 as 705, 706, 707 and 708 respectively.

From a hardware point of view, the system may comprise a specially constructed and configured unit or a conventionally constructed and commercially available computer, such as a PC, notebook or the like, a workstation.

An alternative may provide that the processing is performed remotely from a server also managed by a third party, such as a clinical centre or a hospital or a centre specialised in image processing, or even by the company that has produced and/or distributed the MRI apparatus, a cable communication unit being envisaged, or wireless communication unit using dedicated communication protocols or the usual internet connections, whereby the images acquired by the MRI apparatus are transmitted to the server for processing by the same and the results of the processing are then transmitted by the server to the MRI apparatus or to a local communication station.

This solution has the advantage of having a particularly large database of known cases and, above all, of having a great number of learning cases from the processing processes performed. In addition, the training database optimisation processes and the algorithm training optimisation processes do not have to be performed by individual users' systems, which takes up the users' time, but are performed remotely at the processing server operators.

Figure 6:
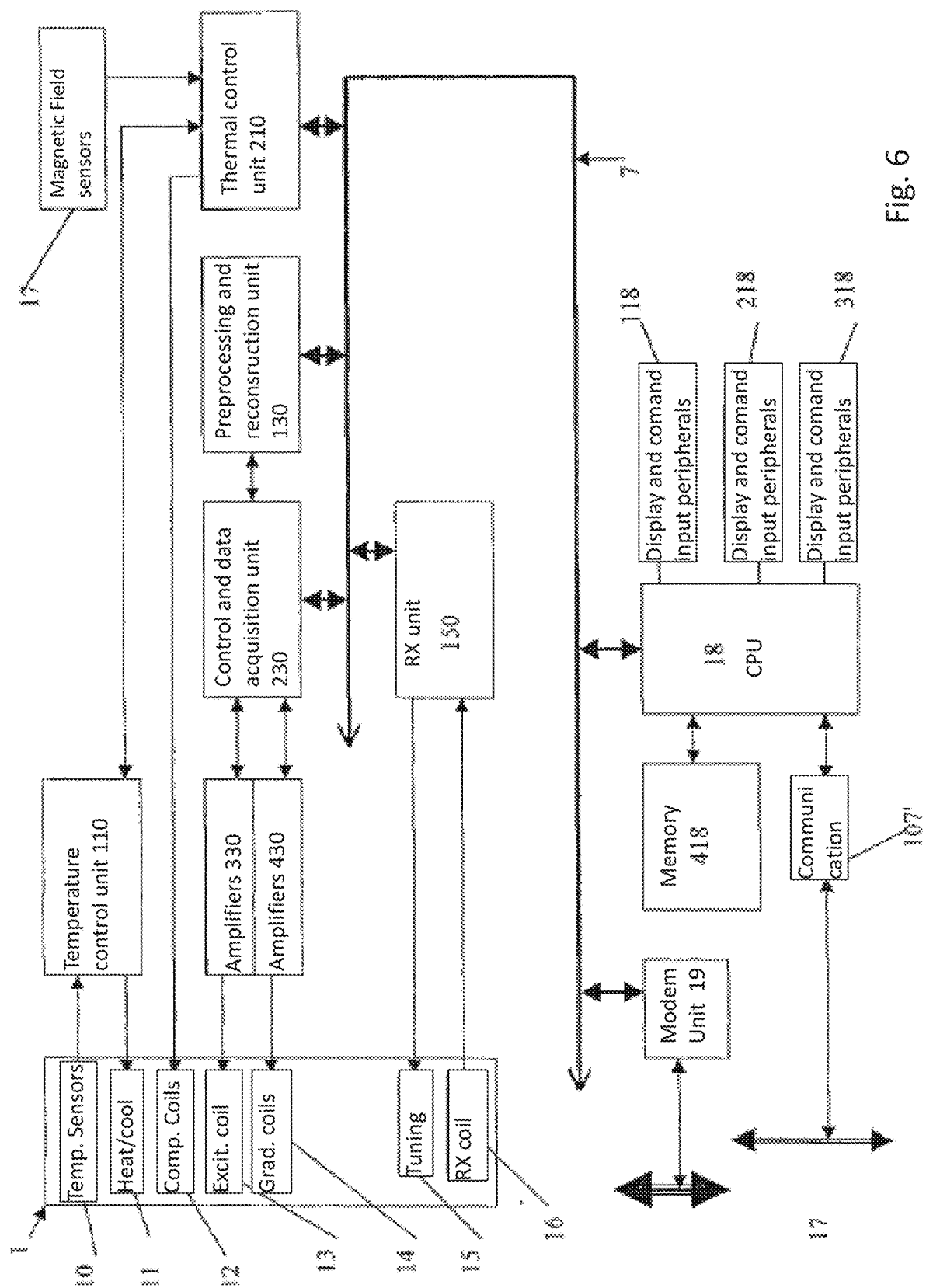
FIG. 6 illustrates a more detailed block diagram of the machine according to FIG. 5.

Referring to FIG. 6, a nuclear magnetic resonance imaging machine comprises an excitation and reception unit comprising a magnetic unit 1. The magnetic unit has permanent or resistive or superconductive magnets for generating a static field in a housing cavity 101 of the patient's body or a part thereof, in particular a limited anatomical district, such as a leg, an arm, the head, etc.

As is generally known, various coils are associated with the static field generating magnet including:
excitation coils for the excitation of nuclear spins
coils of generation of magnetic gradients for the selection of the section plane along which the image is detected, for the encoding of the nuclear spins, in order to univocally identify the signals emitted at a pre-established spatial position and therefore univocally assign the information received to a pre-established pixel of a matrix of pixels constituting the displayed image;
receiving coils for receiving magnetic resonance echoes.

In addition, other means are provided, such as, for example, sensors for temperature control and/or heat supply or heat generation means and heat dissipation means for setting and maintaining a predetermined working temperature, etc.

All the elements described above are known and common to nuclear magnetic resonance imaging machines of any type and size, whether so-called "total body" machines, i.e., machines designed to accommodate all or a large part of the patient's body, or so-called dedicated machines designed to accommodate only some limbs or limited parts or areas of the patient's body. The geometry of the magnetic structure, i.e. the cavity housing the body under examination or part of it, can also be of any type, and in particular can be open, C or U-shaped or made up of two poles separated by columns, or of the so-called closed annular type.

The machine illustrated is a machine with a closed magnetic structure, i.e. annular, and the cavity is open only in correspondence to the two leading sides transversal to the axis.

The magnetic unit is generally associated with a couch or a couch chair, which is indicated by 2 and which may have any construction. In particular, the chair or the couch 2 may have a structure suitable for forming closable housing niches as is schematically illustrated in FIG. 6.

The magnetic unit or magnetic structure, with the aforementioned components, is associated with control, command and processing units which have the function of controlling and adjusting the various components of the magnetic structure and of receiving and processing the echo signals in order to extract information useful for reconstructing from them an image made up of a set of luminous image points so-called pixels which have brightness and/or colour correlated univocally with the information received and position correlated with the position in the part of the body under examination from which an echo signal has been emitted.

In particular, and generically, the magnetic unit is associated with an electronic unit 3 for controlling the excitation and reception devices, a unit 4 for entering commands to the excitation and reception unit, a unit 5 for displaying, processing images and a unit 6 for archiving and storing.

The unit 3 for controlling the excitation and reception devices is housed at least partly in the case of the magnetic unit 1 and/or possibly also at least partly in the structure of the lounger 2, in a part 202, for example a support column made in the manner of an electrical cabinet.

On the other hand, the units 4 for inputting commands to the excitation and receiving unit, 5 for displaying, processing images and 6 for archiving and storing are partly included as hardware peripherals and partly as software programs in a conventional type of personal computer.

The communication between the unit 3 housed in the magnetic unit case and/or in the bed structure 2 with the units 4, 5, 6 of the control console constituted by the personal computer is performed by means of a communication bus indicated with 7.

The communication bus can be of any type, such as, for example, a standard communication bus of the ethernet type or also of the scsi, usb, or other type, and which allows multiplexed communication of several units with each other.

The implementation of the interfaces with bus 7 on the individual units 3, 4, 5, 6, is currently known once the type of bus to be used has been established.

In an, the personal computer or workstation further constitutes a system as described in the s of FIG. 3 or 4. In this case, the various units identified in the figures of these s are implemented in the form of software units comprising programs which encode instructions for the personal computer or workstation processor(s) and peripheral devices thereof to operate according to the functions of the operating units described in the s of FIG. 3 or 4.

Figure 7:
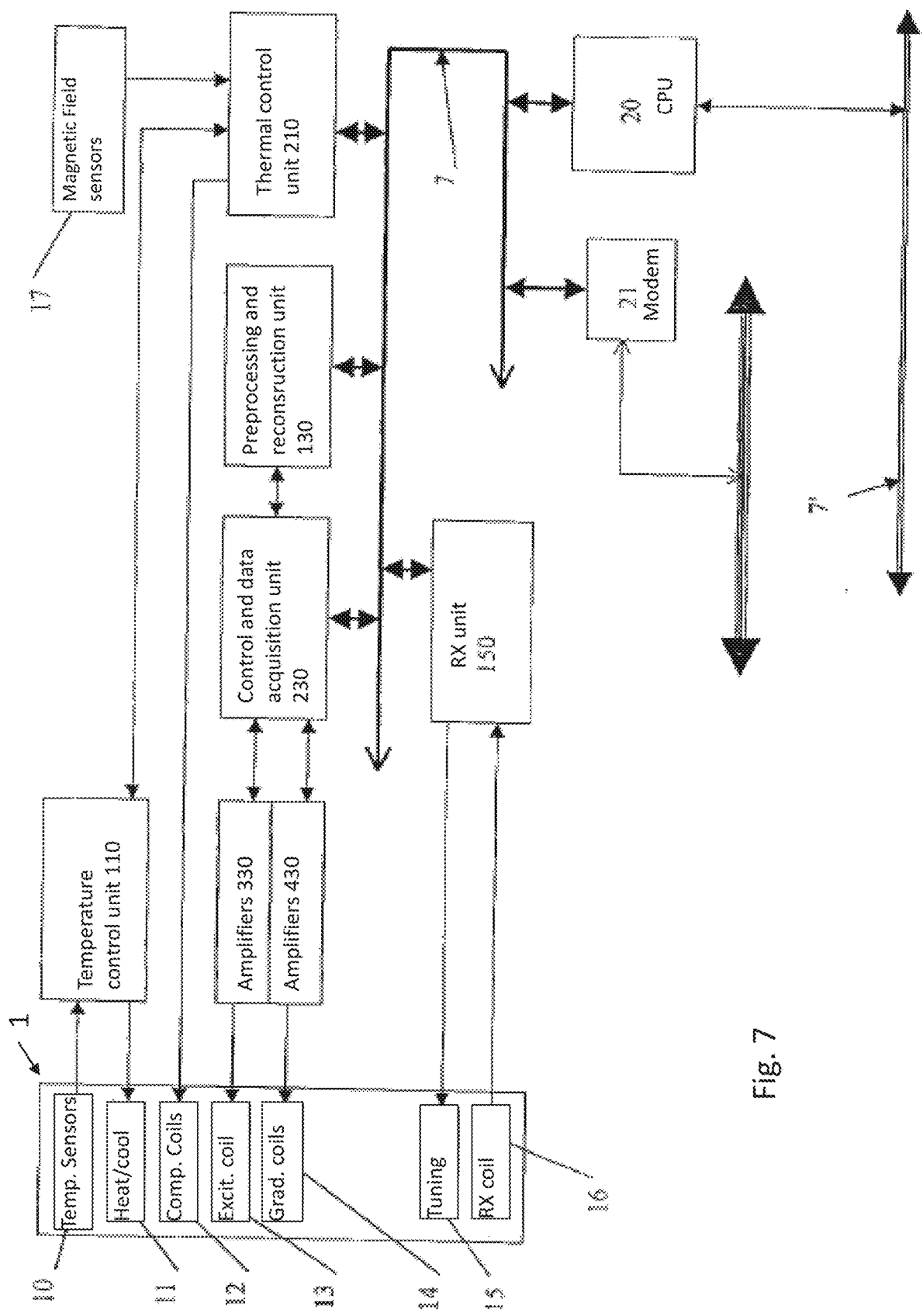
FIG. 7 illustrates a block diagram of a variant of the machine according to FIGS. 5 and 6, wherein the machine is controlled by a central network unit and not by a dedicated computer.

FIG. 7 illustrates in greater detail what is generically described with reference to FIG. 6. The magnetic unit 1 comprises as indicated in the figure various components, namely, in addition to the static field generation magnets, temperature sensors 10, heating and/or cooling means 11, at least one magnetic compensation coil 12, at least one transmission or excitation coil 13, one or more gradient coils 14 tuning means 15 and at least one receiving coil 16 one or more magnetic field sensors 17.

The temperature sensors and the heater and/or cooler means are controlled by a temperature control unit 110 comprising sensor signal reading means 10 and heater and/or cooler power supply means 11 which are controlled by a thermal control unit 210 on the basis of the actual temperature detected and the comparison of this with pre-set nominal values.

The thermal and magnetic control unit also controls the compensation coil 13 to correct the static magnetic field with reference to the variations induced in the same by external magnetic fields and on the basis of the actual field values detected by the magnetic field sensors 17. A supervisory, pre-processing and reconstruction unit 130 controls a control and data acquisition unit 230 which in turn controls the amplifiers 330 and 430 respectively of the signal supplied to the transmission coil 13 or excitation and to the gradient coil(s) 14.

A receiving unit 150, on the other hand, is responsible for tuning 15 the receiving coil 16 and identifying the receiving coil 16, as well as receiving the data collected by said receiving coil 16.

Said units are contained within the magnetic unit case completely or at least partially and/or in a closable niche of the lounger structure 2 completely or at least partially.

The supervision, pre-processing and reconstruction units 130, the control and acquisition unit 230, as well as the thermal and magnetic control unit 110 and the reception unit 150 communicate with each other and/or with the further units by means of a bus 7.

More particularly, said units communicate with the CPU 18 of a usual personal computer provided with usual peripherals in the desired or necessary quantity and type.

Connected to the CPU 18 are display and command input peripherals indicated by 118, 218, 318, as well as at least one mass memory, for storage and a memory for specific image processing and display software, for programs encoding the functions of one or more of the operating units of an image processing system for separating images relating to water and fat, for example according to one of the implementation forms of FIG. 3 or 4 and which are summarised in a single box and indicated globally by 418. The CPU 18 can also in turn communicate 107' with a local communication relay 7', such as an internal hospital LAN or intranet or internet network, or any suitable type. The communication bus 7 is also connected with a modem unit 19 that allows connection to a local network and/or to other machines present and connected to the local network by means of a telephone line or other communication line, also of wireless type. This redundancy not only allows communication with local networks at other sites, but also provides an alternative way of connecting to the local LAN network if the network interfaces have temporary communication failures. The communication interface may alternatively be used to communicate with a remote server which performs the operations relating to the processing unit, for example in accordance with one of the forms of execution of FIGS. 3 and 4 as described above.

As is evident from the foregoing, the communication bus is not only provided between the individual units, but also extends within the units themselves, allowing great freedom of configuration and use of the machine, as well as the addition of functional units with new type functions and/or the replacement of old type units with more modern type units. The ease of replacement for both machine upgrading and repair is obvious. As long as the signals are coded according to the bus used, any unit can connect to the communication bus 7 and be able to exchange data and commands with other units.

The construction of the machine according to the invention also allows other configurations which can be very advantageous both from an economic point of view and from an organisational and management point of view. In fact, the connection of the various units to each other by means of a conventional data bus makes it possible to control several machines, even of different types, but with the same configuration of the processing and control electronics from a single workstation or from a limited number of workstations. It is also possible to envisage a system comprising several machines organised in groups of machines, each group having a single dedicated console in the form of a conventional computer, the conventional computers associated with each group being configured as client computers accessing a server computer via a network. In this case, the server computer may contain a large number of different programmes for controlling the detection and/or image processing and reconstruction procedures, such as a database of nuclear magnetic resonance image acquisition sequences, a database of signal filtering and/or signal processing procedures for modulating the definition and/or contrast and/or signal-to-noise ratio and/or detection times, while the client computers can access the server databases to retrieve from the above databases the programs and/or procedures for detection and/or treatment of images and also the procedures for separation of the water/fat images according to one or more of the embodiments of the method of the present invention described above.

In this way, client computers can be configured more economically, especially with regard to memories and graphics sections. It is also possible to provide local display media, such as monitors or printers of limited quality, by associating the higher quality media with the server. This constitutes a considerable saving of resources, making it possible to purchase, for example, monitors and/or other display media such as printers or similar of higher quality.

An example of a machine configuration according to the invention suitable for this configuration is illustrated in FIG. 7. In this figure, identical reference numbers are used for identical functions or identical means. As is evident from the comparison with FIG. 6, the units expressly dedicated to the control of the magnetic unit and to the reception of the echo signals, as well as to their processing for the extraction of the image information data, are identical to those already described with reference to FIG. 7.

Unlike the previous example, however, the machine does not have a dedicated console but comprise a local CPU unit that manages communications between the internal bus 7 and the communication bus, for example a LAN network or similar indicated with 20. A modem 21, if present, allows communication by means of telephone type lines.

The local CPU 20, to which local memories may be associated, accesses via the LAN network a local computer which constitutes the units described in FIG. 2 and which is intended to manage several machines. The local computer, in turn, can, as already mentioned, constitute a client of a general server computer controlling several groups of machines.

The presence of an internal management CPU 20 does not constitute a real cost burden, both due to the low cost of the CPUs and to the fact that this configuration makes it possible to limit the number of computers dedicated to controlling the machines.

In addition, the local CPU may also be able to manage local peripherals, such as storage, display, printing and command input devices.

It should be noted that the presence of a local CPU 20 is also not an impediment, should this be desired to the fact of providing one or more machines with a dedicated console.

With reference to FIGS. 6 to 7, a further feature of the invention should be noted, and which constitutes an advantage. In fact, in dedicated machines it is often necessary to provide supports external to the machine for limbs or limb parts that are not housed in the sensing cavity or compartment. In this case, for example when imaging a knee, the patient's other leg would have to remain outside the magnetic structure 1. In order to allow a comfortable position for the patient, the magnetic unit case has side extensions 201 which are the housing cabinets for the units mounted in the magnetic unit case and at the same time supports for the limbs not housed in the detection cavity. Therefore, the need to create housing space for the electronic units stably associated with the magnetic unit case are combined with the need to create supports external to the magnetic unit case itself, whereby any increased space requirements determined by the invention are in any case compensated for by the exploitation of the same as support elements.

The invention claimed is:

1. A method for separate acquisition and output of diagnostic images in nuclear magnetic resonance imaging based on signals from water and fat, which method comprises:
    a) defining at least a slice of an image that passes through a body, or an area of a body, under examination with a pre-established relative orientation;
    b) acquiring for at least said slice, or for at least a part of all said slices when there are more than one slice, at least an anatomical image in nuclear magnetic resonance along said slice;
    (c) performing, for at least said slice or for at least part of all of said slices when there are more than one, and for each pixel or voxel of the nuclear magnetic resonance image acquired along said slice, a separation of signal components corresponding to an intensity of said pixel or voxel resulting from water within the body under examination from those signal components resulting from fat tissues in said body under examination;
    (d) generating for at least said slice, or for at least part of all of said slices when there are more than one, an image called water-only which is generated on the basis of signal components of MRI signals resulting from water-only separated in step (c);
    (e) generating for at least a slice, or for at least part of all of said slices, when there are more than one, an image called fat-only which is generated on the basis of signal components of the MRI signals resulting from fat-only separated in step (c);
    (f) sorting images related to any single slice in a sequence that for each slice provides firstly for said anatomical image(s) and afterward said water-only image(s) followed by said fat-only image(s);
    g) sorting images related to any single slice according by position order of said slices when there are more than one, and wherein
    h) the separation of signal components corresponding to intensity of said pixel or voxel resulting from water within the body under examination from those signal components resulting from fat tissues in said body under examination of step c) being performed by a machine learning algorithm that uses automatic learning to configure the machine learning algorithm process based on feedback mechanisms involving training and testing processes with image data; and
    using a parameter analysis operator to reduce a number of image pixels, the parameter analysis operator configured to determine an appearance of pixels where an operator identifies regions of the image to be analyzed, wherein parameters of pixel appearance are related to signals resulting from water or fat, submitting to an elaboration process by means of the machine learning algorithm only pixels that fall within the range of said parameters of pixel appearance that are functional to determining the image as resulting from water or fat.

2. A method according to claim 1, in which a separation algorithm of images related to the signal contribution resulting from water and images related to the signal contribution resulting from fat is a classification algorithm.

3. A method according to claim 1, in which pixels or voxels are represented by the corresponding numerical parameter regarding the intensity of pixel or voxel expressed with a metric defined by a grayscale gradation.

4. A method for separate acquisition and output of diagnostic images in nuclear magnetic resonance imaging based on signals from water and fat, which method comprises:
   a) defining at least a slice of an image that passes through a body, or an area of a body, under examination with a pre-established relative orientation:
   b) acquiring for at least said slice or for at least a part of all said slices when there are more than one slice, at least an anatomical image in nuclear magnetic resonance along said slice;
   (c) performing, for at least said slice or for at least part of all of said slices when there are more than one, and for each pixel or voxel of the nuclear magnetic resonance image acquired along said slice, a separation of signal components corresponding to an intensity of said pixel or voxel resulting from water within the body under examination from those signal components resulting from fat tissues in said body under examination;
   (d) generating for at least said slice, or for at least part of all of said slices when there are more than one, an image called water-only which is generated on the basis of signal components of MRI signals resulting from water-only separated in step (c);
   (e) generating for at least a slice, or for at least part of all of said slices when there are more than one, an image called fat-only which is generated on the basis of signal components of the MRI signals resulting from fat-only separated in step (c);
   (f) sorting images related to any single slice in a sequence that for each slice provides firstly for said anatomical image(s) and afterward said water-only image(s) followed by said fat-only image(s);
   g) sorting images related to any single slice according by position order of said slices when there are more than one, and wherein
   h) the separation of signal components corresponding to intensity of said pixel or voxel resulting from water within the body under examination from those signal components resulting from fat tissues in said body under examination of step c) being performed by a machine learning algorithm that uses automatic learning to configure the machine learning algorithm process based on feedback mechanisms involving training and testing processes with image data; and
   prior to step (c) selecting a descriptive parameter of each pixel or voxel of an image, which is a combination of descriptive parameters of one or more boundary pixels or voxels of said parameter weighed according to the distance from said pixel or voxel.

5. A method according to claim 1, wherein a separation algorithm of MRI images resulting from water from those resulting from fat is trained with a training database comprising records related to known cases which comprises pixel or voxel intensity parameters of images related to water and fat and their validation as images resulting from water or fat performed by qualified staff or with state of the art separation techniques.

6. A method according to claim 5, wherein a training database is generated by optimized selection of records from a database of known cases.

7. A method according to claim 6, wherein selection of known cases records for training database generation is performed by means of a genetic algorithm being fitness value of classification obtained by a trained classifier with a certain training database application criterion of the selection based on the fitness value.

8. A method according to claim 1, wherein after an acquisition step of a first MRI image along a predetermined slice, and before the separation step, are provided further steps of:
   acquiring for at least said slice or for at least part or all said slices, when these are more than one, an image called water-only that is generated on the basis of MRI signals resulting from water-only;
   acquiring for at least said slice or for at least part or all said slices, when these are more than one, an image called fat-only that is generated on the basis of MRI signals resulting from fat-only;
   while a validation step is provided in which the machine learning algorithm is configured and used for the validation classification of the images acquired as related to the only signal component resulting from water or related to the only signal component resulting from the fat tissues existing in the body under examination.

9. A method according to claim 1, wherein it is provided to perform a sequence of images acquisition of water and fat that involves the acquisition of a sequence of two anatomical MRI images and the following acquisition of two images whose signals are related to water and an image wherein signals are related to fat, said images being sorted according to a sequence that provides firstly two anatomical images and afterwards the image related to water and the image related to fat, being said sequence kept fixed for all acquisitions of MRI images, while the above mentioned machine learning algorithm, i.e. the predictive or classification algorithm is used to identify which of the two images acquired after the two anatomical images is related to water and which is related to fat and to generate the above mentioned sequence of images.

10. A method for separate acquisition and output of diagnostic images in nuclear magnetic resonance imaging based on signals from water and fat, which method comprises:
   a) defining at least a slice of an image that passes through a body, or an area of a body, under examination with a pre-established relative orientation;
   b) acquiring for at least said slice, or for at least a part of all said slices when there are more than one slice, at least an anatomical image in nuclear magnetic resonance along said slice;
   (c) performing, for at least said slice or for at least part of all of said slices when there are more than one, and for each pixel or voxel of the nuclear magnetic resonance image acquired along said slice, a separation of signal components corresponding to an intensity of said pixel or voxel resulting from water within the body under examination from those signal components resulting from fat tissues in said body under examination;
   (d) generating for at least said slice, or for at least part of all of said slices when there are more than one, an image called water-only which is generated on the basis of signal components of MRI signals resulting from water-only separated in step (c);
   (e) generating for at least a slice, or for at least part of all of said slices when there are more than one, an image called fat-only which is generated on the basis of signal components of the MRI signals resulting from fat-only separated in step (c);
   (f) sorting images related to any single slice in a sequence that for each slice provides firstly for said anatomical image(s) and afterward said water-only image(s) followed by said fat-only image(s);

g) sorting images related to any single slice according by position order of said slices when there are more than one, and wherein h) the separation of signal components corresponding to intensity of said pixel or voxel resulting from water within the body under examination from those signal components resulting from fat tissues in said body under examination of step c) being performed by a machine learning algorithm that uses automatic learning to configure the machine learning algorithm process based on feedback mechanisms involving training and testing processes with image data wherein there is provided a phase of image shrinking and where said phase of image shrinking occurs before a phase of processing the parameters describing the appearance of pixels or voxels wherein the intensity is expressed in a grayscale.

11. A method according to claim 10, wherein there is provided a step of merging together in one or more pixels or voxels, pixels or voxels belonging to the original image that have the same intensity with reference to the measuring meter according to said grayscale.

12. A method according to claim 11, wherein the determination of the condition of identity is performed by subdividing the gradation scale in a plurality of grey scale fields wherein each field corresponds to an intensity value field that is focused on a predetermined intensity value and has a maximum limit value and a minimum limit value, which fields define the intensity values of the pixels or voxels to be considered identical and therefore to be merged together in a single pixel or voxel or in several pixels or voxels in order to obtain a variable and selectable reduction or a reduction to a predetermined size of the size of the images that are to be processed.

13. A method according to claim 12, wherein said maximum value and said minimum value of fields in which the grayscale or intensity scale is subdivided are variable so as to vary the size of the image having small dimensions.

14. A method according to claim 1, wherein image size is selected according to the fitness of the classification result of a prior execution of the separation algorithm on images having different small size compared to images originally acquired.

15. A method according to claim 1, wherein the reduced image size is defined by a genetic algorithm.

16. A system for MRI images separation resulting from water or fat where said system comprises an integrated processing unit in an MRI apparatus that uses the same processing units provided for controlling the MRI apparatus, or where said system comprises a separate processing unit communicating with an MRI apparatus being said system comprised of a local computer or a remote server that is configured to control the system to perform the method of claim 1.

17. A system according to claim 16, for MRI images separation resulting from water and fat where said system comprises an integrated processing unit in an MRI apparatus that uses the same processing units provided for controlling the MRI apparatus.

18. A system according to claim 16, for MRI images separation resulting from water and fat where said system comprises a separate processing unit communicating with an MRI apparatus being said system comprised of a local computer or a remote server.

* * * * *